US012807590B2

(12) United States Patent
Igawa

(10) Patent No.: US 12,807,590 B2

(45) Date of Patent: Nov. 24, 2026

(54) ORGANIC COMPOUND AND ELECTROCHROMIC ELEMENT

(71) Applicant: CANON KABUSHIKI KAISHA, Tokyo (JP)

(72) Inventor: Satoshi Igawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 678 days.

(21) Appl. No.: 18/189,081

(22) Filed: Mar. 23, 2023

(65) Prior Publication Data

US 2023/0416222 A1 Dec. 28, 2023

(30) Foreign Application Priority Data

Mar. 30, 2022 (JP) ................................ 2022-056594

(51) Int. Cl.

| | |
|---|---|
| ***C07D 401/04*** | (2006.01) |
| ***C09K 9/02*** | (2006.01) |
| ***C09K 11/06*** | (2006.01) |
| ***G02F 1/03*** | (2006.01) |
| ***G02F 1/163*** | (2006.01) |

(52) U.S. Cl.

CPC .............. *C07D 401/04* (2013.01); *C09K 9/02* (2013.01); *C09K 11/06* (2013.01); *G02F 1/0311* (2013.01); *G02F 1/163* (2013.01); *C09K 2211/1029* (2013.01)

(58) Field of Classification Search

CPC ......... C07D 401/04; C09K 9/02; C09K 11/06

See application file for complete search history.

(56) References Cited

U.S. PATENT DOCUMENTS

2020/0233277 A1* 7/2020 Kubo .................... G02F 1/1503

FOREIGN PATENT DOCUMENTS

| | | | | | |
|---|---|---|---|---|---|
| CN | 102666778 | A | * | 9/2012 | C09K 9/02 |
| JP | 2017021327 | A | | 1/2017 | |
| JP | 2017206499 | A | | 11/2017 | |
| JP | 2018508034 | A | | 3/2018 | |
| JP | 2019070788 | A | | 5/2019 | |

OTHER PUBLICATIONS

English Translation JP2018508034A (Year: 2018).*

* cited by examiner

*Primary Examiner* — Lucy P Chien

(74) *Attorney, Agent, or Firm* — Canon.U.S.A., Inc. IP Division

(57) ABSTRACT

An organic compound is represented by formula (1):

(1)

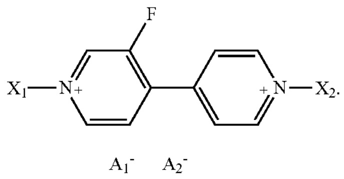

In formula (1), $X_1$ and $X_2$ are each independently selected from the group consisting of an alkyl group, an aryl group, and an aralkyl group. $A_1^-$ and $A_2^-$ each independently represent a monovalent anion.

22 Claims, 6 Drawing Sheets

ORGANIC COMPOUND AND ELECTROCHROMIC ELEMENT

BACKGROUND OF THE INVENTION

Field of the Invention

The present disclosure relates to an organic compound and an electrochromic element using the organic compound.

Description of the Related Art

An electrochromic (hereinafter, may be referred to as "EC") property is a property that optical absorption properties (the coloration state and light transmittance) of a substance change due to reversible progress of an electrochemical oxidation-reduction reaction, so that the color tone of the substance changes.

EC elements are elements that include a pair of electrodes and an EC layer disposed between the pair of electrodes. In EC elements, a voltage is applied to the pair of electrodes to adjust the amount of light passing through the EC layer. That is, EC elements can control the transmittance of light.

Various materials such as inorganic materials, polymer materials, and organic low-molecular-weight materials are known as EC materials used in EC layers.

These materials have been used for application of EC elements to, for example, light-control mirrors of automobiles and electronic paper. These EC devices utilize the property that various color tones can be displayed depending on materials selected. In utilizing EC elements, it is necessary to develop materials having various color tones. For example, in the case of an application to full-color displays and the like, materials that are colored to cyan, magenta, and yellow are necessary. In the case of an application to a wider range of uses, coloring materials having various color tones are necessary.

Japanese Patent Laid-Open No. 2017-206499 (PTL 1) discloses a pyridine derivative having good redox stability.

However, the compound disclosed in PTL 1 has room for improvement in terms of drive voltage when used in an EC element.

SUMMARY OF THE INVENTION

The present disclosure provides an organic compound that exhibits an EC property at a lower voltage.

An organic compound according to the present disclosure is represented by formula (1):

(1)

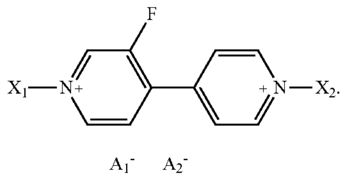

In formula (1), $X_1$ and $X_2$ are each independently selected from the group consisting of a substituted or unsubstituted alkyl group, a substituted or unsubstituted aryl group, and a substituted or unsubstituted aralkyl group. $A_1^-$ and $A_2^-$ each independently represent a monovalent anion.

Further features of the present disclosure will become apparent from the following description of exemplary embodiments with reference to the attached drawings.

DESCRIPTION OF THE EMBODIMENTS

Figure 1:
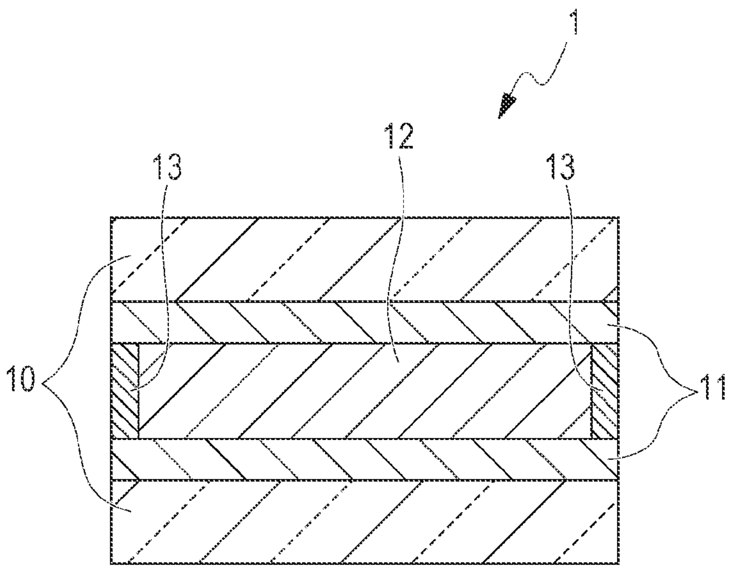
FIG. 1 is a schematic sectional view of an example of an electrochromic element according to an embodiment.

In the present specification, examples of halogen atoms include, but are not limited to, a fluorine atom, a chlorine atom, a bromine atom, and an iodine atom.

An alkyl group may be an alkyl group having 1 to 20 carbon atoms. The alkyl group may have 1 to 8 carbon atoms and may be linear, branched, or cyclic. Examples thereof include, but are not limited to, a methyl group, an ethyl group, a normal propyl group, an isopropyl group, a normal butyl group, a tert-butyl group, a secondary butyl group, an octyl group, a cyclohexyl group, a 1-adamantyl group, and a 2-adamantyl group. Examples of substituents that the alkyl group may have include, but are not limited to, a halogen atom, an ester group, and a cyano group. A hydrogen atom in the alkyl group may be substituted with a halogen atom, in particular, a fluorine atom. A carbon atom that the alkyl group has may be substituted with an ester group or a cyano group.

An aryl group may be an aryl group having 6 to 24 carbon atoms. Examples thereof include, but are not limited to, a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group. The aryl group may have, as a substituent, at least one of a halogen atom, an alkyl group having 1 to 8 carbon atoms, or an alkoxy group having 1 to 8 carbon atoms. A hydrogen atom in the alkyl group or the alkoxy group may be substituted with a halogen atom, in particular, a fluorine atom.

An aralkyl group may be an aralkyl group having 7 to 20 carbon atoms. Examples thereof include, but are not limited to, a benzyl group and a phenethyl group. The aralkyl group may have a substituent, and specifically may have an alkyl group having 1 to 8 carbon atoms or an alkoxy group having 1 to 8 carbon atoms. A hydrogen atom in the alkyl group or the alkoxy group may be substituted with a halogen atom, in particular, a fluorine atom.

Examples of an ester group include, but are not limited to, carboxylic acid ester groups, sulfonic acid ester groups, and phosphonic acid ester groups.

In the present specification, "becoming colored" means that the transmittance at a specific wavelength decreases.

The "organic compound that becomes colored when reduced" refers to an organic compound having a lower visible-light transmittance when reduced than a visible-light transmittance when oxidized.

(1) Organic Compound

First, an organic compound according to the present disclosure will be described.

The organic compound according to the present disclosure is an organic compound represented by general formula (1) below and has an EC property. Thus, the organic compound according to the present disclosure can also be referred to as an EC compound. The organic compound according to the present disclosure is an organic compound that becomes colored when reduced.

(1)

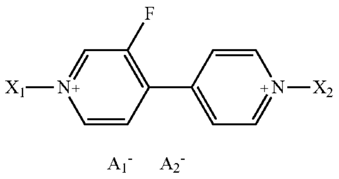

In general formula (1), $X_1$ and $X_2$ are each independently selected from a substituted or unsubstituted alkyl group, a substituted or unsubstituted aryl group, and a substituted or unsubstituted aralkyl group.

$X_1$ and $X_2$ may have an alkyl group having 1 to 8 carbon atoms, an aryl group having 6 to 14 carbon atoms, or an aralkyl group having 7 to 10 carbon atoms, and may have a n-heptyl group, a phenyl group, or a benzyl group. $X_1$ and $X_2$ may have different structures or the same structure and may have the same structure in view of the ease of synthesis.

$X_1$ and $X_2$ may have an adsorptive group or an acid ester group thereof for adsorption to an electrode. The electrode may be a porous electrode. Specific examples of the adsorptive group or acid ester group thereof include a carboxyl group and carboxylic acid ester groups, a sulfonic acid group and sulfonic acid ester groups, a phosphonic acid group and phosphonic acid ester groups, and trialkoxysilyl groups. To improve solubility in an organic solvent, $X_1$ and $X_2$ may have an ionic group such as a pyridinium group or a quinolinium group. In one embodiment, $X_1$ and $X_2$ may have a phosphonic acid group, a carboxylic acid ester group, a phosphonic acid ester group, or a pyridinium group.

$A_1^-$ and $A_2^-$ each independently represent a monovalent anion.

Examples of the monovalent anion represented by $A_1^-$ and $A_2^-$ include anions such as $PF_6^-$, $ClO_4^-$, $BF_4^-$, $AsF_6^-$, $SbF_6^-$, $CF_3SO_3^-$, and $(CF_3SO_2)_2N^-$; and halogen anions such as $Br^-$, $Cl^-$, and $I^-$. $A_1^-$ and $A_2^-$ each may represent $PF_6^-$, $ClO_4^-$, $BF_4^-$, $CF_3SO_3^-$, $(CF_3SO_2)_2N^-$, $Br^-$, or $I^-$ and, in particular, may represent $PF_6^-$ or $BF_4^-$.

$A_1^-$ and $A_2^-$ may represent different anions or the same anion and may represent the same anion in view of the ease of synthesis.

The organic compound represented by general formula (1) has the following features.

(1-1) The organic compound has a fluorine atom at the 3-position of 4,4'-bipyridine and thus can suppress a decrease in the reduction potential.

(1-2) The organic compound has a fluorine atom at the 3-position of 4,4'-bipyridine and thus can reduce a change in the absorption spectrum due to the environmental temperature.

(1-3) The organic compound has a fluorine atom at the 3-position of 4,4'-bipyridine and thus has high transparency when dissolved in a solvent.

These features will be described below.

(1-1) The organic compound has a fluorine atom at the 3-position of 4,4'-bipyridine and thus can suppress a decrease in the reduction potential.

The organic compound according to the present disclosure is an organic compound that has a fluorine atom at the 3-position of 4,4'-bipyridine and thus that can suppress a decrease in the reduction potential. PTL 1 discloses an organic compound having an alkyl group or an alkoxy group at the 3-position of 4,4'-bipyridine. Since an alkyl group or an alkoxy group acts as an electron-donating group on 4,4'-bipyridine, the reduction potential is further lowered (has a negative value having a large absolute value). Thus, the use of such an organic compound in an EC element increases the drive voltage. In contrast, the organic compound according to the present disclosure has a fluorine atom at the 3-position of 4,4'-bipyridine. Since a fluorine atom acts as an electron-withdrawing group on 4,4'-bipyridine, the decrease in the reduction potential can be suppressed. Specifically, the organic compound according to the present disclosure is a compound that exhibits an EC property at a lower voltage. Thus, the use of the organic compound according to the present disclosure in an EC element lowers the drive voltage.

(1-2) The organic compound has a fluorine atom at the 3-position of 4,4'-bipyridine and thus can reduce a change in the absorption spectrum due to the environmental temperature.

The organic compound according to the present disclosure is an organic compound that has a fluorine atom at the 3-position of 4,4'-bipyridine and thus that can reduce a change in the absorption spectrum due to the environmental temperature. It is considered that a fluorine atom has the highest electronegativity and thus is capable of suppressing dimerization due to intermolecular repulsion. Therefore, the organic compound according to the present disclosure can reduce a change in the absorption spectrum due to the environmental temperature.

(1-3) The organic compound has a fluorine atom at the 3-position of 4,4'-bipyridine and thus has high transparency in the bleached state.

The organic compound according to the present disclosure is an organic compound that has high transparency in the bleached state. Since the organic compound according to the present disclosure has a fluorine atom at the 3-position of 4,4'-bipyridine, the organic compound has a twist structure. The conjugation length of the molecule changes due to the twist structure; thus, the absorption wavelength also changes. As a result, in the bleached state, since the absorption of visible light can be reduced, the organic compound has high transparency. Therefore, the organic compound according to the present disclosure can maintain high transparency when dissolved in a solvent.

The method for synthesizing the organic compound according to the present disclosure is not particularly limited, and the organic compound can be synthesized by, for example, methods described below. In the compound represented by general formula (1), when at least one of $X_1$ or $X_2$ is an alkyl group or an aralkyl group, an organic compound represented by general formula (2) and a halide are caused to react with each other in a predetermined solvent. Subsequently, an anion-exchange reaction is performed with a salt containing a desired anion in a predetermined solvent to obtain the organic compound. When at least one of $X_1$ or $X_2$ is an aryl group, the organic compound can be obtained by causing an organic compound represented by general formula (2) to react with a hypervalent iodine compound, and subsequently performing an anion-exchange reaction with a salt containing an anion in a predetermined solvent. One of the imines alone may be caused to react by selecting the solvent and the reaction temperature. Alternatively, substituents different from each other may be introduced into the two imines by repeating the reactions.

(2)

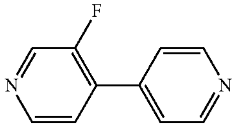

The method for synthesizing the compound represented by general formula (2) is not particularly limited, and the compound can be synthesized by, for example, the following synthetic method.

In the synthetic route, X represents a halogen atom such as Cl, Br, or I.

Intermediate 1 can be synthesized by a coupling reaction of 4-halogenated pyridine having a fluorine atom at the 3-position and 4-pyridylboronic acid.

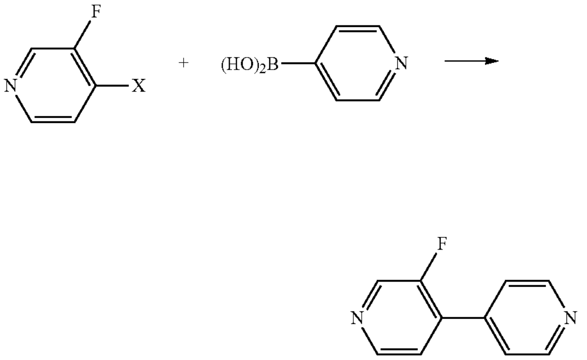

Intermediate 1

Specific structural formulae of the organic compound according to the present disclosure are shown as examples below. However, the compound according to the present disclosure is not limited to these compounds.

A-1

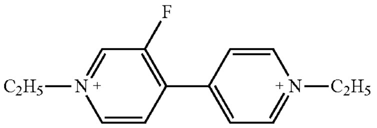

$2(CF_2SO_2)_2N^-$

A-2

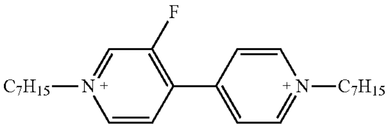

$2I^-$

A-3

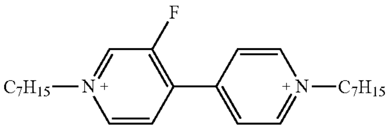

$2PF_6^-$

A-4

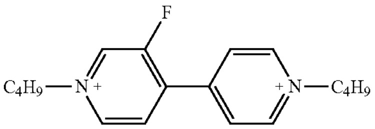

$2CF_3SO_3^-$

A-5

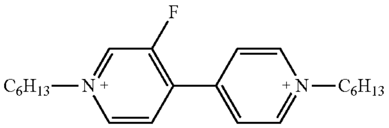

$2BF_4^-$

A-6

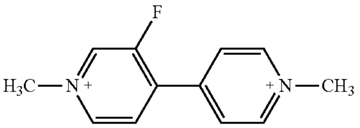

$2PF_6^-$

A-7

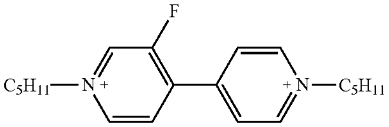

$2(CF_3SO_2)_2N^-$

A-8

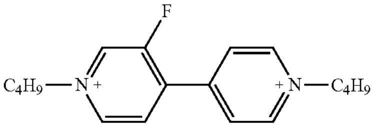

$2ClO_4^-$

-continued
A-9
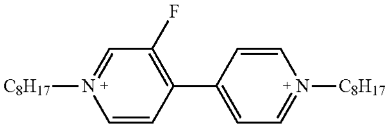
$2ClO_4^-$
A-10
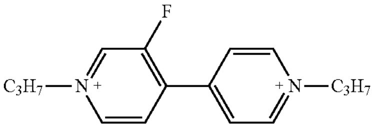
$2Br^-$
B-1
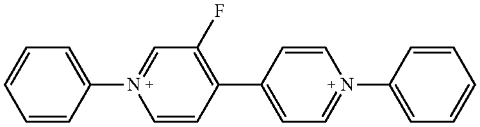
$2PF_6^-$
B-2
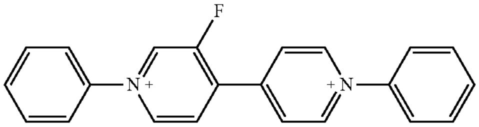
$2(CF_3SO_2)_2N^-$
B-3
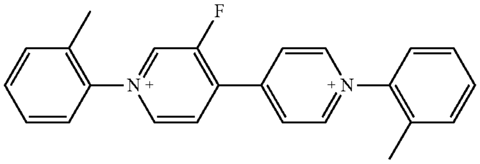
$2(CF_3SO_2)_2N^-$
B-4
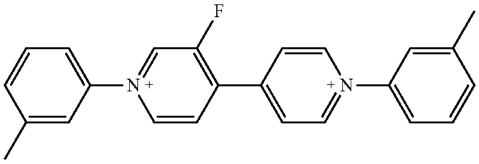
$2CF_3SO_3^-$
B-5
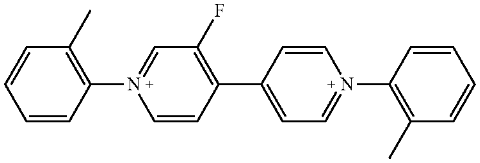
$2PF_6^-$
B-6
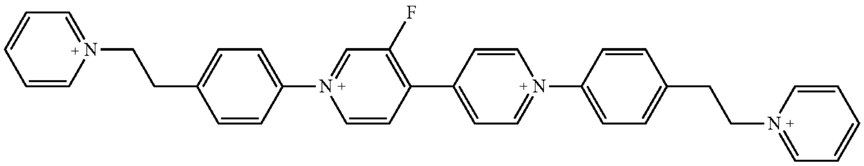
$4(CF_3SO_2)_2N^-$
B-7
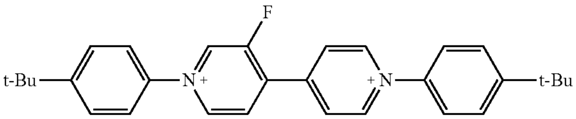
$2(CF_3SO_2)_2N^-$
B-8
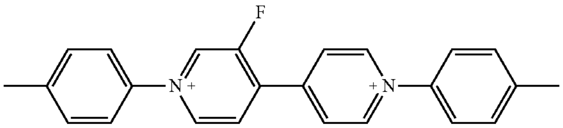
$2(CF_3SO_2)_2N^-$
B-9
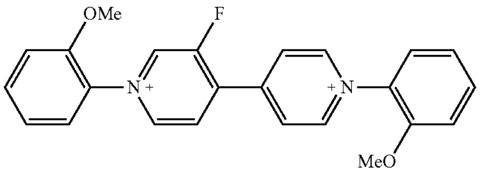
$2PF_6^-$
B-10
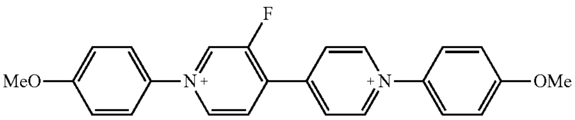
$2BF_4^-$ -continued
B-11
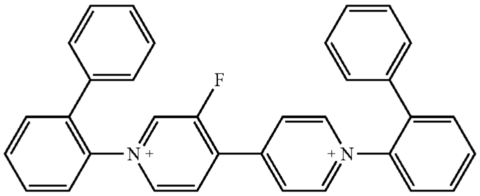
$2(CF_3SO_2)_2N^-$
B-12
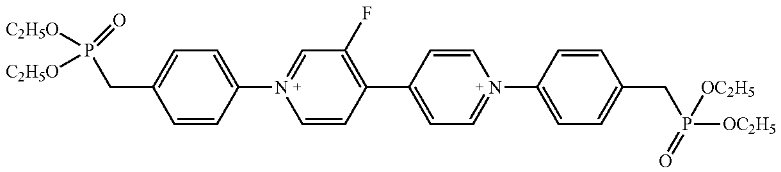
$2(CF_3SO_2)_2N^-$
B-13
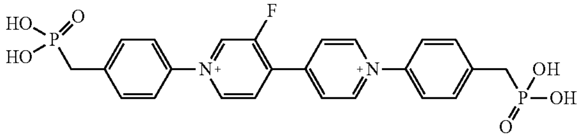
$2(CF_3SO_2)_2N^-$
B-14
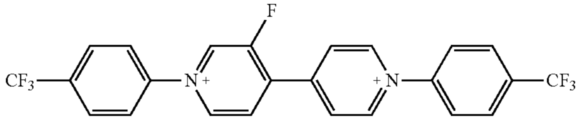
$2PF_6$
C-1
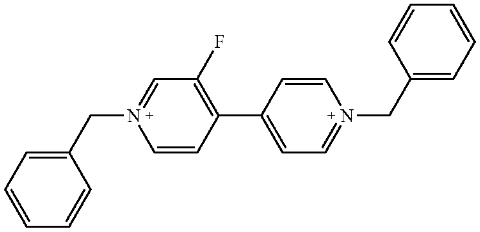
$2Br_2^-$
C-2
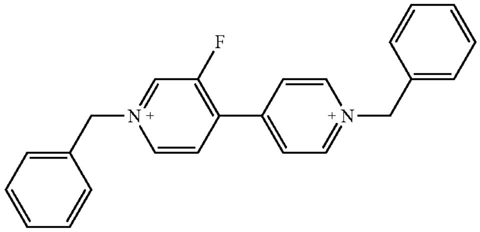
$2BF_4^-$
C-3
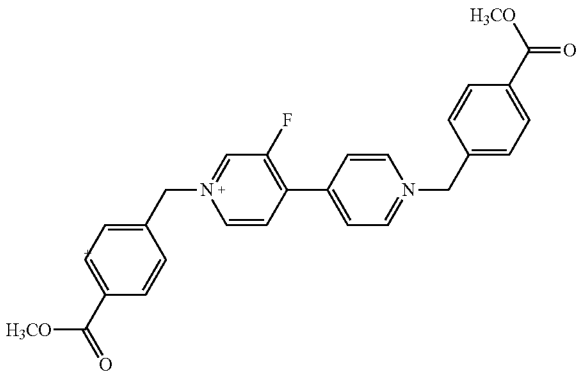
$2(CF_3SO_2)_2^-$
C-4
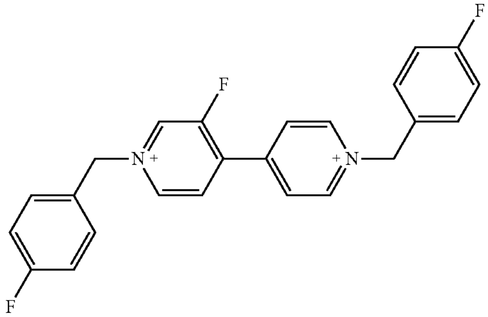
$2CF_3SO_3^-$
D-1
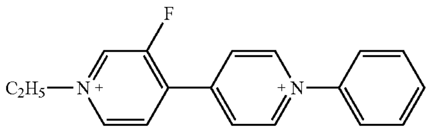
$2PF_6^-$
D-2
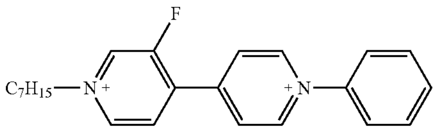
$2CF_3SO_3^-$ -continued

D3

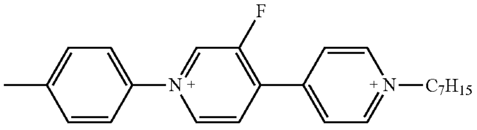

$2(CF_3SO_2)_2N^-$

D-4

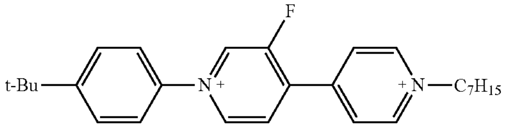

$2CF_3SO_3^-$

D-5

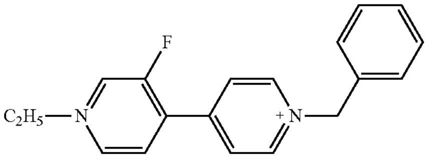

$2PF_6^-$

D-6

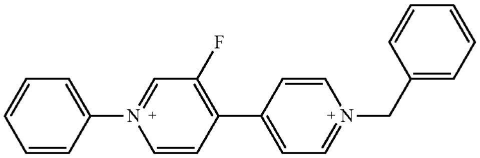

$2PF_6^-$

Among the above exemplary compounds, compounds belonging to group A are a group of compounds in which $X_1$ and $X_2$ have the same structure. Since $X_1$ and $X_2$ have the same structure, these compounds are easily synthesized. In addition, since $X_1$ and $X_2$ are each an alkyl group, good durability is provided.

Among the above exemplary compounds, compounds belonging to group B are a group of compounds in which $X_1$ and $X_2$ have the same structure. Since $X_1$ and $X_2$ have the same structure, these compounds are easily synthesized. In addition, since $X_1$ and $X_2$ are each an aryl group, the absorption wavelength is easily adjusted.

Among the above exemplary compounds, compounds belonging to group C are a group of compounds in which $X_1$ and $X_2$ have the same structure. Since $X_1$ and $X_2$ have the same structure, these compounds are easily synthesized. In addition, since $X_1$ and $X_2$ are each an aralkyl group, the absorption wavelength is easily adjusted.

Among the above exemplary compounds, compounds belonging to group D are a group of compounds in which $X_1$ and $X_2$ have different structures. Therefore, the absorption wavelength is easily adjusted.

Since the above exemplary compounds each have a fluorine atom at the 3-position of 4,4'-bipyridine, the exemplary compounds are compounds having high transparency when dissolved in a solvent.

EC Element

The organic compound according to the present embodiment can be used as an EC layer of an EC element. An EC element according to the embodiment will be described below with reference to the drawings.

An EC element 1 illustrated in FIG. 1 includes a pair of substrates 10, a pair of electrodes 11, and an EC layer 12 disposed between the pair of electrodes. The pair of electrodes 11 is configured so that the distance between the electrodes is fixed by a spacer 13. In this EC element 1, the pair of electrodes 11 is disposed between the pair of the substrates 10. The EC layer 12 contains the organic compound according to the present disclosure. This EC layer 12 may have a layer formed of the organic compound according to the present disclosure and a layer formed of an electrolyte. Alternatively, the EC layer 12 may be provided as a solution containing an EC compound and an electrolyte. In the EC element 1 according to this embodiment, the EC layer 12 may be a solution layer. When the EC layer 12 is a solution layer, the organic compound according to the present disclosure, a solution, and other dissolved substances may be collectively referred to as an EC medium. Components of the EC element 1 according to this embodiment will be described below.

EC Layer 12

The electrolyte is not limited as long as it is a compound that has good solubility in a solvent in the case of an ion dissociative salt, and it is a compound that exhibits high compatibility with the organic compound according to the present disclosure in the case of a solid electrolyte. In particular, an electrolyte having electron-donating properties may be used. These electrolytes may also be referred to as supporting electrolytes. Examples of the electrolyte include inorganic ion salts such as various alkali metal salts and alkaline-earth metal salts, quaternary ammonium salts, and cyclic quaternary ammonium salts. Specific examples thereof include salts of alkali metals of Li, Na, and K such as $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl; and quaternary ammonium salts and cyclic quaternary ammonium salts such as $(CH_3)_4NBF_4$, $(C_2H_5)_4NBF_4$, $(n\text{-}C_4H_9)_4NBF_4$, $(n\text{-}C_4H_9)_4NPF_6$, $(C_2H_5)_4NBr$, $(C_2H_5)_4NClO_4$, and $(n\text{-}C_4H_9)_4NClO_4$.

The solvent in which the organic compound according to the present disclosure and the electrolyte are dissolved is not particularly limited as long as the organic compound and the electrolyte are dissolved therein, and in particular, polar solvents may be used. Specific examples thereof include water and organic polar solvents such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, benzonitrile, dimethylacetamide, methylpyrrolidinone, and dioxolane.

The EC layer 12 used may be one obtained by further incorporating a polymer or a gelling agent to have a high viscosity or a gel form, for example. Such a polymer or gelling agent may also be referred to as a thickener. When a thickener is incorporated to increase the viscosity of the EC medium, the organic compound becomes less likely to form an aggregate, and the temperature dependency of the absorption spectrum can be reduced. Therefore, the EC medium may contain the thickener.

The viscosity of the EC medium is preferably 10 cP or more and 5,000 cP or less and more preferably 50 cP or more and 1,000 cP or less. The viscosity of the EC medium is preferably 150 cP or less, more preferably 100 cP or less, and particularly preferably 65 cP or less. The viscosity of the EC medium is preferably 20 cP or more and more preferably 50 cP or more. A viscosity of the EC medium exceeding 5,000 cP is not preferred because the movement of carriers of the EC medium is suppressed, resulting in a decrease in the rate of reaction of the EC element 1.

The thickener preferably has a weight ratio of 20% by weight or less, more preferably 1% by weight or more and 15% by weight or less, and particularly preferably 5% by weight or more and 10% by weight or less when the total weight of the EC medium is assumed to be 100% by weight.

Examples of the polymer include, but are not particularly limited to, polyacrylonitrile, carboxymethylcellulose, polyvinyl chloride, polyalkylene oxide, polyurethane, polyacrylate, polymethacrylate, polyamide, polyacrylamide, polyester, and NAFION (registered trademark). Polymethyl methacrylate, polyethylene oxide, and polypropylene oxide may be used.

The EC element 1 according to the embodiment may include the organic compound according to the present disclosure and a second organic compound different in type from the organic compound. The second organic compound may be one compound or a plurality of compounds and may be a compound that becomes colored when oxidized, a compound that becomes colored when reduced, or a compound having both the properties. In particular, a compound that becomes colored when oxidized may be contained. The "compound that becomes colored when oxidized" refers to a compound having a lower visible-light transmittance when oxidized than a visible-light transmittance when reduced. However, it is sufficient that the transmittance changes in any portion of the visible light region, and the transmittance need not change over the entire region of visible light.

The organic compound according to the present disclosure can absorb a desired color as an EC element by being combined with a coloring material of another color. The second organic compound in the colored state preferably has an absorption wavelength in a range of 400 nm or more and 800 nm or less, and more preferably has an absorption wavelength in a range of 420 nm or more and 700 nm or less. By combining the organic compound according to the present disclosure with a plurality of second organic compounds, an EC element that absorbs light in the entire visible region and becomes colored in black may also be produced.

The EC element 1 according to this embodiment may include five or more second organic compounds together with the organic compound according to the present disclosure. This is because a filter including the EC element 1 easily evenly absorbs light at each wavelength.

Examples of the second organic compounds that can be used in the EC element 1 according to this embodiment include the following compounds. Examples of the second organic compounds that become colored when oxidized include oligothiophene-based compounds, phenazine-based compounds such as, for example, 5,10-dihydro-5,10-dimethylphenazine and 5,10-dihydro-5,10-diisopropylphenazine, metallocene-based compounds such as ferrocene, tetra-tert-butylferrocene, and titanocene, phenylenediamine-based compounds such as N,N',N,N'-tetramethyl-p-phenylenediamine, and pyrazoline-based compounds such as 1-phenyl-2-pyrazoline.

Examples of the compounds that become colored when reduced include viologen-based compounds such as N,N'-diheptylbipyridinium diperchlorate, N,N'-diheptylbipyridinium ditetrafluoroborate, N,N'-diheptylbipyridinium dihexafluorophosphate, N,N'-diethylbipyridinium diperchlorate, N,N'-diethylbipyridinium ditetrafluoroborate, N,N'-diethylbipyridinium dihexafluorophosphate, N,N'-dibenzylbipyridinium diperchlorate, N,N'-dibenzylbipyridinium ditetrafluoroborate, N,N'-dibenzylbipyridinium dihexafluorophosphate, N,N'-diphenylbipyridinium diperchlorate, N,N'-diphenylbipyridinium ditetrafluoroborate, and N,N'-diphenylbipyridinium dihexafluorophosphate; anthraquinone-based compounds such as 2-ethylanthraquinone, 2-tert-butylanthraquinone, and octamethylanthraquinone; ferrocenium-salt-based compounds such as ferrocenium tetrafluoroborate and ferrocenium hexafluorophosphate; and styryl-based compounds.

In this embodiment, the phenazine-based compound refers to a compound having a 5,10-dihydrophenazine skeleton in the chemical structure or a 5,10-dihydrophenazine derivative having a substituent. For example, hydrogen atoms at the 5- and 10-positions of 5,10-dihydrophenazine may be substituted with alkyl groups such as a methyl group, an ethyl group, and a propyl group or aryl groups such as a phenyl group. The phenazine-based compound may be a 5,10-dihydrophenazine derivative having an alkyl group having 1 to 20 carbon atoms. The phenazine-based compound may be a 5,10-dihydrophenazine derivative having an alkoxy group having 1 to 20 carbon atoms. The phenazine-based compound may be a 5,10-dihydrophenazine derivative having an aryl group having 4 to carbon atoms. The same applies to other compounds, for example, viologen-based compounds.

Among the above compounds, the second organic compound may be any of phenazine-based compounds, metallocene-based compounds, phenylenediamine-based compounds, and pyrazoline-based compounds.

Substrates 10

The substrates 10, in particular, transparent substrates used are formed of, for example, colorless or color glass, tempered glass, or a colorless or color transparent resin. In this embodiment, the transparent substrates may have a visible-light transmittance of 90% or more. Specific examples thereof include polyethylene terephthalate, polyethylene naphthalate, polynorbornene, polyamide, polysulfone, polyethersulfone, polyether ether ketone, polyphenylene sulfide, polycarbonate, polyimide, and polymethyl methacrylate.

Electrodes 11

Examples of materials of the electrodes 11, in particular, transparent electrodes include metals and metal oxides such as indium tin oxide alloys (ITO), fluorine-doped tin oxide (FTO), tin oxide (NESA), indium zinc oxide (IZO), silver oxide, vanadium oxide, molybdenum oxide, gold, silver, platinum, copper, indium, and chromium; silicon-based materials such as polysilicon and amorphous silicon; and carbonaceous materials such as carbon black, graphite, and glassy carbon. Furthermore, conductive polymers whose electrical conductivities are improved by, for example, doping treatment, such as complexes between polystyrene sulfonate and polyaniline, polypyrrole, polythiophene, polyacetylene, polyparaphenylene, or polyethylene dioxythiophene (PEDOT) are also suitably used.

Furthermore, the electrodes 11 may be porous electrodes. The porous electrodes may be formed of a material having a large surface area with a porous shape having fine pores in the surface and inside thereof, a rod shape, a wire shape, or the like. The materials of the porous electrodes may be, for example, metals, metal oxides, or carbon. Suitable examples thereof include metal oxides such as titanium oxide, tin oxide, iron oxide, strontium oxide, tungsten oxide, zinc oxide, tantalum oxide, vanadium oxide, indium oxide, nickel oxide, manganese oxide, and cobalt oxide.

Spacer 13

The spacer 13 is disposed between the pair of electrodes 11 and provides a space for housing, as the EC layer 12, a solution containing the organic compound according to the present disclosure. Specifically, for example, polyimide, polytetrafluoroethylene, polyester, fluororubber, or an epoxy resin may be used. This spacer 13 enables the distance between the electrodes of the EC element 1 to be maintained.

The EC element 1 according to this embodiment may have a liquid injection port formed by the pair of electrodes 11 and the spacer 13. After a composition containing the organic compound according to this embodiment is enclosed from the liquid injection port, the injection port is covered with a sealing member and further hermetically sealed with an adhesive or the like. Thus, an EC element can be provided. The sealing member also has a function of separating the adhesive and the EC medium so as not to be in contact with each other. The shape of the sealing member is not particularly limited and may be a tapered shape such as a wedge shape.

The method for forming the EC element 1 according to this embodiment is not particularly limited and may be a method in which an EC medium prepared in advance so as to contain the organic compound according to the present disclosure is injected into a gap between the pair of electrodes 11 by, for example, a vacuum injection method, an air injection method, or a meniscus method.

Use of EC Element 1

By driving the EC element 1 according to this embodiment, the amount of light passing through the EC element 1 can be adjusted; thus, the EC element 1 is applicable to, for example, optical filters, lens units, image pickup apparatuses, and window members.

Optical Filter

An optical filter according to this embodiment includes the EC element 1 according to the present disclosure and an active element connected to the EC element 1. The optical filter according to the present disclosure may include a peripheral device. The active element may be connected to the EC element 1 either directly or indirectly with another element therebetween. Examples of the active element include TFT elements and MIM elements. In the optical filter according to the present disclosure, the active element drives the EC element 1 to adjust the amount of light passing through the EC element 1. The transistor may contain, in the active region, an oxide semiconductor such as InGaZnO.

Figure 2:
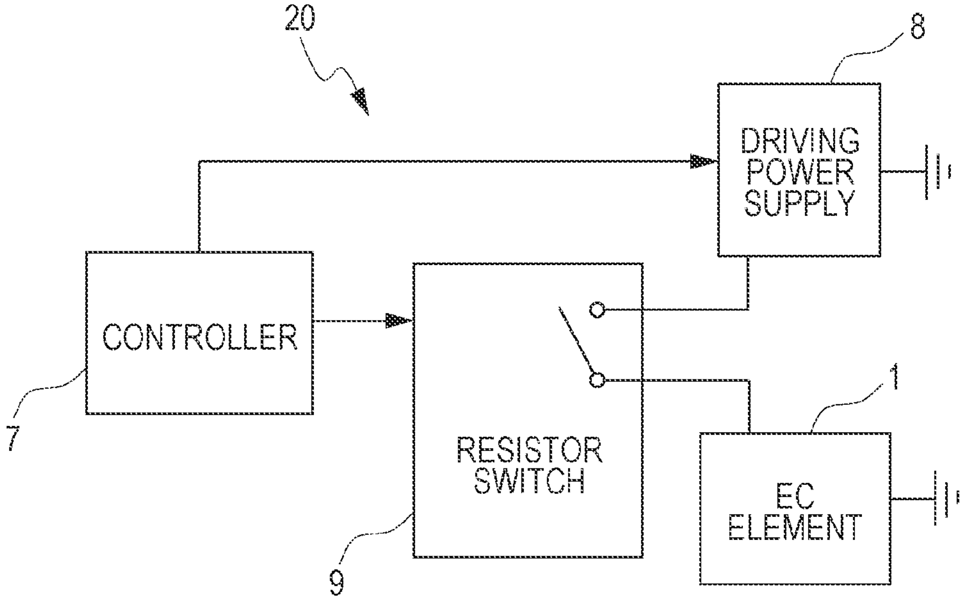
FIG. 2 is a schematic diagram illustrating an example of a drive device including an electrochromic element according to an embodiment.

The optical filter according to this embodiment includes an EC element 1 according to the present disclosure and a drive device 20 connected to the EC element 1. FIG. 2 is a schematic diagram illustrating an example of the drive device 20 and the EC element 1 that the drive device 20 drives. The drive device 20 according to this embodiment includes a driving power supply 8, a resistor switch 9, and a controller 7.

The driving power supply 8 applies, to the EC element 1, a voltage (hereinafter, referred to as a "drive voltage") necessary for causing an electrochemical reaction of the EC medium containing the organic compound according to the present disclosure. When the EC layer 12 contains a plurality of EC materials, the absorption spectrum may change in some cases due to the difference in oxidation-reduction potential between the EC materials and the difference in molar absorbance coefficient. Therefore, the drive voltage may be a constant voltage. The start of application or the holding of the drive voltage is performed by a signal of the controller 7. In this embodiment, a state where a constant voltage is applied is maintained during a period in which the light transmittance of the EC element 1 is controlled.

As the method for controlling the transmittance of the EC element 1 by the controller 7, a method suitable for the element used is employed. Specifically, examples thereof include a method of inputting predetermined conditions into the EC element 1 in accordance with a desired set value of the transmittance, and a method of comparing the set value of transmittance with the transmittance of the EC element 1, and inputting conditions selected so as to satisfy the set value. Examples of parameters to be changed include a voltage, a current, and a duty ratio. In the present specification, the term "duty ratio" refers to a ratio of the duration of application of the voltage relative to a single period of the pulse voltage waveform. The controller 7 enables the coloring density of the EC element to be changed by changing the voltage, the current, or the duty ratio.

In the embodiment, publicly known methods may be employed to change the voltage, change the current, and modulate the pulse width. The pulse width may also be modulated as described below.

The resistor switch 9 switches, in a closed circuit including the driving power supply 8 and the EC element 1, between a resistor R1 and a resistor R2 (which are not illustrated) having a higher resistance than the resistor R1 to establish a series connection. The resistance of the resistor R1 may be at least lower than the highest impedance of the element closed circuit and may be 10Ω or less. The resistance of the resistor R2 may be higher than the highest impedance of the element closed circuit and may be 1 MΩ or more. The resistor R2 may be the air. In this case, although the closed circuit is strictly an open circuit, the circuit is considered to be a closed circuit because the air can be regarded as the resistor R2.

The controller 7 transmits a switching signal to the resistor switch 9 to control switching between the resistor R1 and the resistor R2. When the resistor R1 is connected, the EC element 1 becomes colored. When the resistor R2 is connected, the EC element 1 become bleached. While the resistor R2 is connected, the EC material undergoes self-bleaching. This self-bleaching occurs due to, for example, instability of radical species of the EC material generated in the colored state, diffusion of the radical species into a counter electrode having a different potential, and collision of radical species of an anode material and radical species of a cathode material in a solution.

Lens Unit

A lens unit according to this embodiment includes the above-described optical filter according to the present disclosure and an image pickup optical system having a plurality of lenses. The lens unit according to this embodiment may be arranged such that light that has passed through the optical filter according to the present disclosure passes through the image pickup optical system or arranged such that light that has passed through the image pickup optical system passes through the optical filter according to the present disclosure. In particular, the optical filter according to this embodiment may be disposed on the optical axis of the lenses.

Image Pickup Apparatus

An image pickup apparatus according to this embodiment includes the above-described optical filter according to the present disclosure and a light-receiving element configured to receive light that has passed through the optical filter. Specific examples of the image pickup apparatus include cameras, video cameras, and camera-equipped mobile phones. The image pickup apparatus may have a structure in which a body including a light-receiving element, and a lens unit including a lens can be separated from each other. Herein, in such a case where the body and the lens unit of the image pickup apparatus can be separated from each other, a structure in which an optical filter separated from the image pickup apparatus is used during image capturing is also included within the scope of the present disclosure. The optical filter may be disposed, for example, outside of the lens unit, between the lens unit and the light-receiving element, or between a plurality of lenses (when the lens unit includes a plurality of lenses).

Figure 3A:
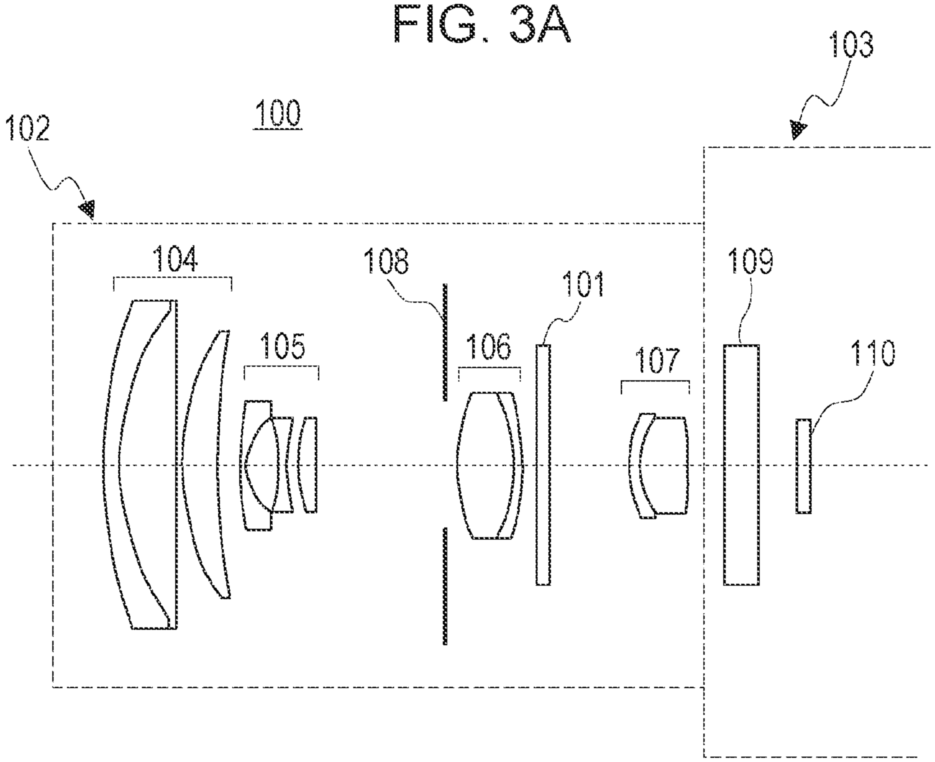
FIG. 3A is a schematic view of an example of an image pickup apparatus in which an optical filter is disposed in a lens unit.
Figure 3B:
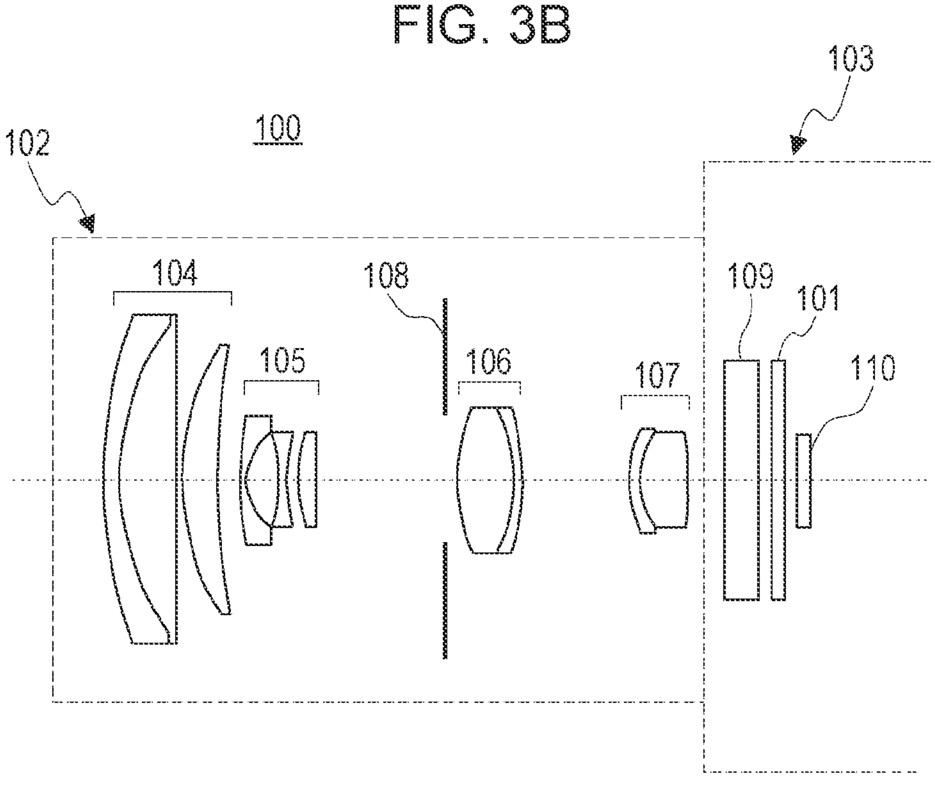
FIG. 3B is a schematic view of an example of an image pickup apparatus in which an optical filter is disposed in an image pickup unit.

FIG. 3A is a schematic view of an example of an image pickup apparatus in which an optical filter is disposed in a lens unit. FIG. 3B is a schematic view of an example of an image pickup apparatus in which an optical filter is disposed in an image pickup unit.

An image pickup apparatus 100 is an image pickup apparatus that includes a lens unit 102 and an image pickup unit 103. The lens unit 102 includes an optical filter 101 and an image pickup optical system having a plurality of lenses or lens groups. The optical filter 101 is the above-described optical filter 101 according to the present disclosure.

The lens unit 102 is, for example, a rear-focus zoom lens that performs focusing behind a diaphragm. The lens unit 102 sequentially includes, from the photographic subject (object) side, a first lens group 104 having a positive refractive power, a second lens group 105 having a negative refractive power, a third lens group 106 having a positive refractive power, and a fourth lens group 107 having a positive refractive power, in total, four lens groups and an optical filter 101. In this embodiment, for example, the distance between the second lens group 105 and the third lens group 106 may be changed to vary the magnification, and some lens groups of the fourth lens group 107 may be moved to perform focusing.

The lens unit 102 includes, for example, an aperture diaphragm 108 between the second lens group 105 and the third lens group 106, and the optical filter 101 between the third lens group 106 and the fourth lens group 107. The lens unit 102 is arranged such that light passing through the lens unit 102 passes through the lens groups 104 to 107, the aperture diaphragm 108, and the optical filter 101, and the aperture diaphragm 108 and the optical filter 101 can be used to adjust the amount of light.

The lens unit 102 may be detachably connected to the image pickup unit 103 via a mount member (not illustrated).

In this embodiment, the optical filter 101 is disposed between the third lens group 106 and the fourth lens group 107 in the lens unit 102; however, the image pickup apparatus 100 is not limited to this configuration. For example, the optical filter 101 may be disposed in front of (on the photographic subject side of) or behind (on the image pickup unit 103 side of) the aperture diaphragm 108. Alternatively, the optical filter 101 may be disposed in front of or behind any of the first to fourth lens groups 104 to 107 or may be disposed between lens groups. When the optical filter 101 is disposed at a position at which light converges, for example, the area of the optical filter 101 can be advantageously reduced.

The configuration of the lens unit 102 is also not limited to the configuration described above and can be appropriately selected.

For example, instead of the rear-focus system, an inner-focus system that performs focusing before the diaphragm or another system may be employed. In addition, special lenses such as a fisheye lens and a macro lens other than the zoom lens may also be used.

The image pickup unit 103 includes a glass block 109 and a light-receiving element 110. The glass block 109 is a glass block serving as a low-pass filter, a face plate, or a color filter. The light-receiving element 110 is a sensor unit that receives light that has passed through the lens unit, and an image pickup element such as a CCD or a CMOS may be used. Alternatively, the light-receiving element 110 may be an optical sensor such as a photodiode, and an element that acquires and outputs information on the intensity or wavelength of light can be appropriately used.

As illustrated in FIG. 3A, when the optical filter 101 is incorporated in the lens unit 102, the drive device 20 may be disposed within the lens unit 102 or outside the lens unit 102. When the drive device 20 is disposed outside the lens unit 102, the EC element 1 within the lens unit 102 and the drive device 20 are connected to each other through wiring to perform drive control.

In the above-described configuration of the image pickup apparatus 100, the optical filter 101 is disposed within the lens unit 102. However, the present disclosure is not limited to this configuration, and the optical filter 101 may be disposed at an appropriate position within the image pickup apparatus 100 as long as the light-receiving element 110 is disposed so as to receive light that has passed through the optical filter 101.

In the above-described configuration of the image pickup apparatus 100, the optical filter 101 is disposed within the lens unit 102. However, the configuration is not limited to this, and the image pickup unit 103 may include the optical filter 101, as illustrated in FIG. 3B. In FIG. 3B, the optical filter 101 is disposed in front of (on the photographic subject side of) the light-receiving element 110. When the image pickup unit 103 includes the optical filter 101 therein, a lens unit 102 connected thereto need not include the optical filter 101. Thus, an image pickup apparatus capable of controlling light can be provided using an existing lens unit 102.

The image pickup apparatus 100 according to this embodiment is applicable to products including a combination of light-amount adjustment and a light-receiving element. For example, the image pickup apparatus can be used for cameras, digital cameras, video cameras, and digital camcorders, and is also applicable to products including image pickup apparatuses such as mobile phones, smartphones, PCs, and tablets.

According to the image pickup apparatus 100 according to this embodiment, when the optical filter 101 is used as a light-control member, the amount of light controlled can be appropriately changed by a single filter, and consequently, advantages in reducing the number of members and saving space are provided.

Window

A window according to this embodiment includes a pair of substrates, an EC element according to the present disclosure disposed between the pair of substrates, and an active element connected to the EC element according to the present disclosure. In the window according to this embodiment, a driving method for driving the EC element 1 may be a method of adjusting, with the active element connected to the EC element 1, the amount of light that has passed through the EC element 1, but the method is not limited to this. Examples of the active element include TFT elements and MIM elements. The transistor may contain, in the active region, an oxide semiconductor such as InGaZnO. The window according to this embodiment may also be referred to as a transmittance-variable window.

Figure 4A:
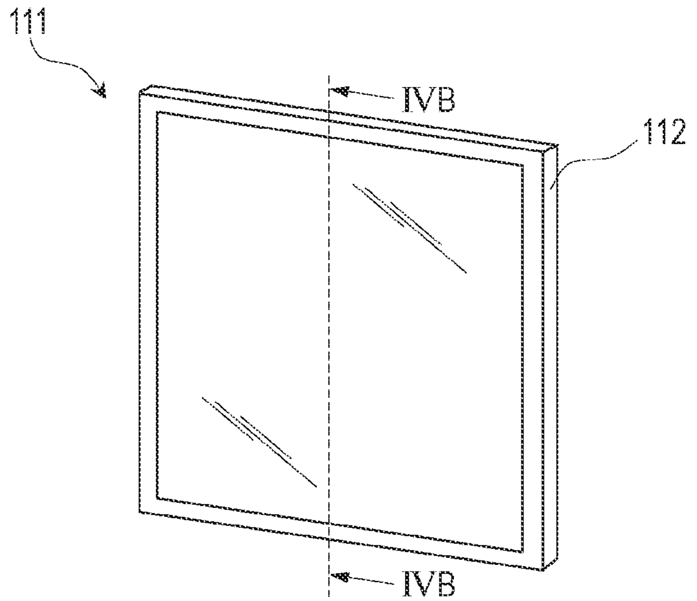
FIG. 4A is a schematic view illustrating a window that uses an EC element according to an embodiment.
Figure 4B:
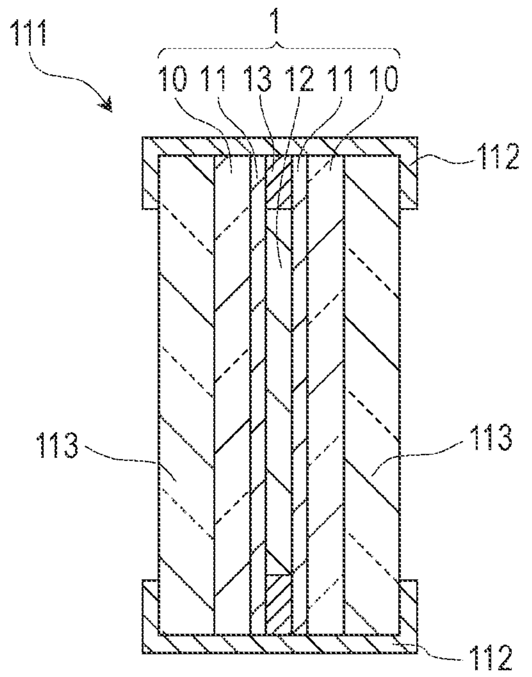
FIG. 4B is a schematic sectional view taken along line IVB-IVB in FIG. 4A.

As illustrated in FIG. 4B, a light-control window 111 of this embodiment includes an EC element 1, transparent plates 113 that sandwich the EC element 1, and a frame 112 that surrounds and integrates the entirety. The EC element 1 has a drive device (not illustrated). The drive device may be disposed within the frame 112 in an integrated manner or may be disposed outside the frame 112 and connected to the EC element 1 through wiring.

The transparent plates 113 may be composed of any material having a high light transmittance, and may be composed of a glass material considering the use as a window. In FIG. 4B, the EC element 1 is a constituent member independent of the transparent plates 113; however, for example, the substrates 10 of the EC element 1 may be regarded as the transparent plates 113.

The frame 112 may be composed of any material. Any member covering at least part of the EC element 1 in an integrated manner may be regarded as a frame.

The light-control window can be used for, for example, adjusting the amount of solar light entering in a room during the day. The light-control window can be used for adjusting the amount of heat besides the amount of solar light, and thus can be used to control the brightness and temperature in the room. The light-control window can also be used as a shutter in order to block the view from the outside to the inside of the room. Such a light-control window is also applicable to, in addition to glass windows for buildings, windows of vehicles, such as automobiles, trains, airplanes, and ships, and filters for display surfaces of clocks and mobile phones.

A reflective member may be disposed on one side of the electrochromic element in the optical path.

Such a window is referred to as an electrochromic mirror and includes a pair of substrates, an EC element 1 according to the present disclosure disposed between the pair of substrates, an active element connected to the EC element 1 according to the present disclosure, and a reflective member. The electrochromic mirror may be installed in, for example, an automobile as an anti-glare mirror.

As described above, the EC element 1 containing the organic compound represented by general formula (1) in the EC layer 12 can be used in an optical filter, a lens unit, an image pickup apparatus, a window, and the like. In the optical filter, the lens unit, the image pickup apparatus, and the window according to this embodiment, the organic compound represented by general formula (1) is used alone or in combination with an EC compound having coloring absorption in a different wavelength range to thereby provide various absorption colors. In addition, since the optical filter, the lens unit, the image pickup apparatus, and the window according to this embodiment each include the organic compound represented by general formula (1), transparency in the bleached state can be improved.

EXAMPLES

The present disclosure will be described below by way of Examples. However, the present disclosure is not limited to these Examples.

Example 1 (Synthesis of Exemplary Compound A-2)

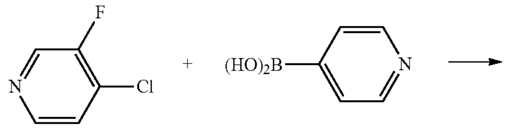

-continued

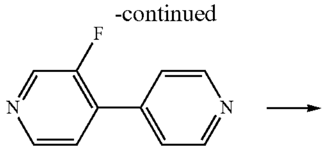

Intermediate 1

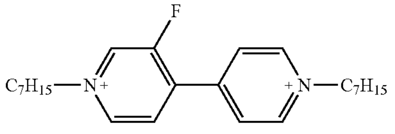

2I$^-$

A-2

In a reaction vessel, 3-fluoro-4-chloropyridine hydrochloride (0.47 g, 3.6 mmol), 4-pyridylboronic acid (0.65 g, 5.3 mmol), tris(dibenzylideneacetone)dipalladium(0) (65 mg, 0.07 mmol), tricyclohexylphosphine (45 mg, 0.16 mmol), tripotassium phosphate (n-hydrate) (2 g), dioxane (10 mL), and water (6 mL) were charged and stirred under heating and refluxing under a nitrogen atmosphere for eight hours. After completion of the reaction, the reaction liquid was concentrated and then extracted with ethyl acetate. The organic layer was washed with water, dried over magnesium sulfate, and then dried and solidified under reduced pressure. The resulting product was purified by silica gel column chromatography (eluant:chloroform/methanol=30/1) to obtain 0.54 g of intermediate 1 (yield: 86%).

In a reaction vessel, 174 mg (1.0 mmol) of intermediate 1, 678 mg (3.0 mmol) of 1-iodoheptane, and 5 mL of acetonitrile were charged and stirred at 80° C. for 16 hours. After completion of the reaction, ethyl acetate was added, and precipitated crystals were filtered and washed with ethyl acetate to obtain 484 mg of exemplary compound A-2 (yield: 77%).

The structure of this compound was confirmed by $^1$H NMR measurement. $^1$H NMR (DMSO-$d_6$, 500 MHz) δ (ppm): 9.76 (d, 1H), 9.38 (d, 2H), 9.28 (d, 1H), 8.65 (t, 1H), 8.97 (d, 1H), 8.57 (d, 2H), 4.71 (t, 4H), 2.00 (m, 4H), 1.34 (m, 8H), 1.28 (m, 8H), (m, 6H)

Example 2 (Synthesis of Exemplary Compound A-3)

Exemplary compound A-2 (125 mg, 0.2 mmol) was dissolved in water. An aqueous solution in which 300 mg of potassium hexafluorophosphate was dissolved was added dropwise, and stirring was performed at room temperature for three hours. The precipitated crystals were filtered and sequentially washed with isopropyl alcohol and diethyl ether to obtain 119 mg of exemplary compound A-3 (yield: 90%).

The structure of this compound was confirmed by $^1$H NMR measurement. $^1$H NMR (DMSO-$d_6$, 500 MHz) δ (ppm): 9.76 (d, 1H), 9.38 (d, 2H), 9.28 (d, 1H), 8.65 (t, 1H), 8.97 (d, 1H), 8.57 (d, 2H), 4.71 (t, 4H), 2.00 (m, 4H), 1.34 (m, 8H), 1.28 (m, 8H), (m, 6H)

Example 3 (Synthesis of Exemplary Compound B-1

Intermediate 1 (174 mg, 1.0 mmol), diphenyliodonium bromide (2.17 g, 6.0 mmol), copper(II) acetate monohydrate (18 mg, 0.10 mmol), and N,N-dimethylformamide (3 mL) were added to a reaction vessel, and a reaction was conducted at 100° C. for 20 hours. After completion of the reaction, vacuum concentration was performed, and acetonitrile was added. The precipitated solid was collected by filtration and dissolved in 10 mL of water. To this solution, an aqueous solution in which 200 mg of ammonium hexafluorophosphate was dissolved was added dropwise, and stirring was performed at room temperature for three hours. The precipitated crystals were filtered and sequentially washed with water, isopropyl alcohol, and diethyl ether to obtain 221 mg of exemplary compound B-1 (yield: 36%).

The structure of this compound was confirmed by $^1H$ NMR measurement. $^1H$ NMR ($CD_3CN$, 500 MHz) δ (ppm): 9.37 (m, 1H), 9.23 (d, 2H), 9.13 (d, 1H), 8.58 (m, 3H), 7.84 (m, 10H)

Example 4 (Synthesis of Exemplary Compound C-2)

In a reaction vessel, 174 mg (1.0 mmol) of intermediate 1, 513 mg (3.0 mmol) of benzyl bromide, and 5 mL of acetonitrile were charged and stirred at 80° C. for two hours. After completion of the reaction, ethyl acetate was added, and precipitated crystals were filtered and washed with ethyl acetate to obtain 622 mg of exemplary compound C-1 (yield: 92%).

Exemplary compound C-1 (135 mg, 0.2 mmol) was dissolved in water. An aqueous solution in which 300 mg of sodium tetrafluoroborate was dissolved was added dropwise, and stirring was performed at room temperature for three hours. The precipitated crystals were filtered and sequentially washed with isopropyl alcohol and diethyl ether to obtain 119 mg of exemplary compound C-2 (yield: 90%).

The structure of this compound was confirmed by $^1H$ NMR measurement. $^1H$ NMR ($CD_3CN$, 500 MHz) δ (ppm): 9.09 (d, 1H), 9.00 (d, 2H), 8.91 (d, 1H), 8.33 (m, 10H), 5.87 (d, 4H)

Example 5 (Production and Characteristic Evaluation of Electrochromic Element Using Exemplary Compound A-3)

Tetrabutylammonium hexafluorophosphate serving as an electrolyte was dissolved at a concentration of 0.1 M in propylene carbonate. Exemplary compound A-3 of Example 2 was then dissolved at a concentration of 40.0 mM to prepare an EC medium.

Subsequently, an insulating layer ($SiO_2$) was formed on four edge portions of a pair of glass substrates with transparent conductive films (ITO). A PET film (Melinex S (registered trademark) manufactured by DuPont Teijin Films, 125 μm in thickness) for defining the distance between the substrates was placed between the pair of glass substrates with transparent electrode films. Subsequently, the glass substrates and the PET film were bonded together with an epoxy-based adhesive to achieve sealing such that an injection port for injecting the EC medium was left. In this manner, an empty cell with an injection port was produced.

Next, the EC medium prepared by the above operation was injected from the injection port by a vacuum injection method, and the injection port was then sealed with an epoxy-based adhesive to produce an EC element.

The EC element immediately after the production exhibited a transmittance of about 80% over the entire visible-light region and had high transparency.

Figure 5:
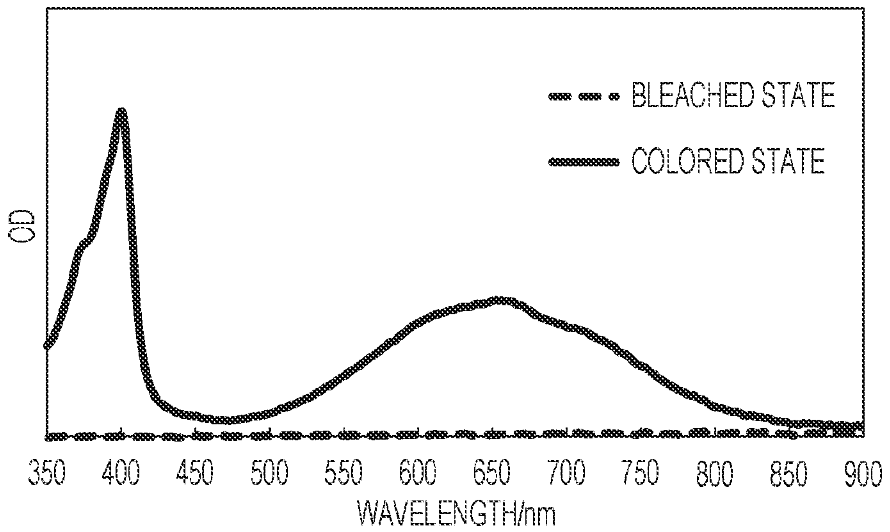
FIG. 5 is a graph showing ultraviolet-visible absorption spectra of exemplary compound A-3 in a colored state and a bleached state.

Upon application of a voltage of 1.1 V to this element, the element exhibited absorption derived from the reduced species of exemplary compound A-3, and the element became colored. Upon further application of −0.5 V, the element was bleached. This element can reversibly change between the colored state and the bleached state. FIG. 5 shows ultraviolet-visible absorption spectra of the element produced in Example 5. As a light source, a DH-20005 deuterium-halogen light source manufactured by Ocean Optics, Inc. was used.

Example 6 (Production and Characteristic Evaluation of Electrochromic Element Using Exemplary Compound B-1)

Figure 6:
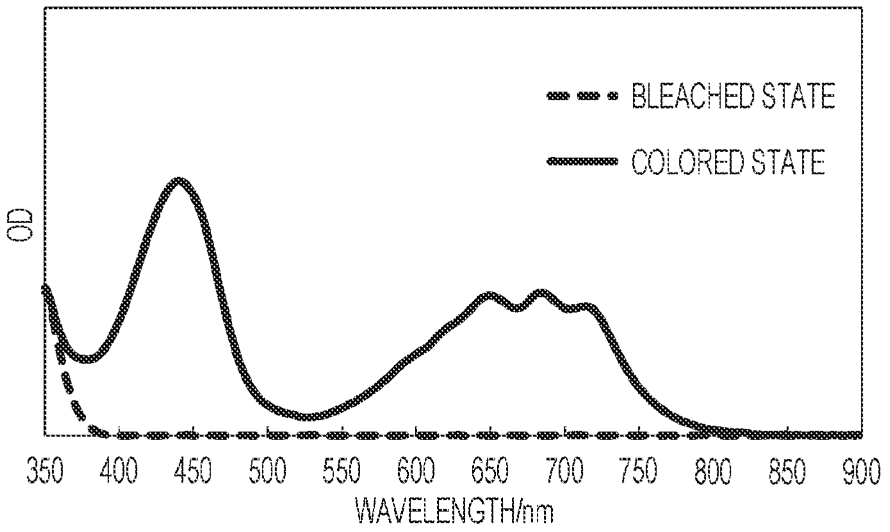
FIG. 6 is a graph showing ultraviolet-visible absorption spectra of exemplary compound B-1 in a colored state and a bleached state.

An element was produced by the same method as in Example 5 except that exemplary compound B-1 was used instead of exemplary compound A-3 in Example 5. Upon application of a voltage of 1.0 V to the element of this Example, the element exhibited absorption derived from the reduced species of exemplary compound B-1, and the element became colored. Upon further application of −0.5 V, the element was bleached, demonstrating reversible coloring and bleaching. This element can reversibly change between the colored state and the bleached state. FIG. 6 shows ultraviolet-visible absorption spectra of the element produced in Example 6.

Example 7 (Production and Characteristic Evaluation of Electrochromic Element Using Exemplary Compound C-2)

Figure 7:
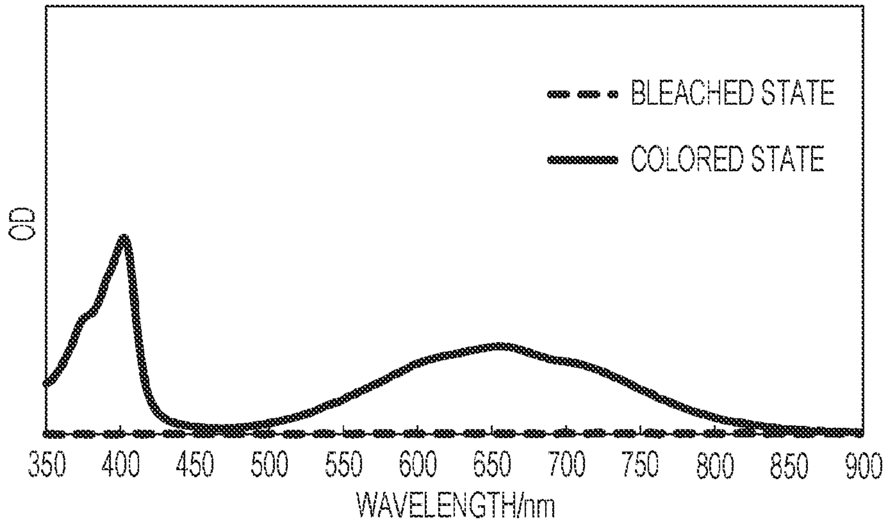
FIG. 7 is a graph showing ultraviolet-visible absorption spectra of exemplary compound C-2 in a colored state and a bleached state.

An element was produced by the same method as in Example 5 except that exemplary compound C-2 was used instead of exemplary compound A-3 in Example 5. Upon application of a voltage of 1.1 V to the element of this Example, the element exhibited absorption derived from the reduced species of exemplary compound C-2, and the element became colored. Upon further application of −0.5 V, the element was bleached, demonstrating reversible coloring and bleaching. This element can reversibly change between the colored state and the bleached state. FIG. 7 shows ultraviolet-visible absorption spectra of the element produced in Example 7.

Example 8 (Temperature Characteristic Evaluation of Electrochromic Element Using Exemplary Compound A-3)

Figure 8:
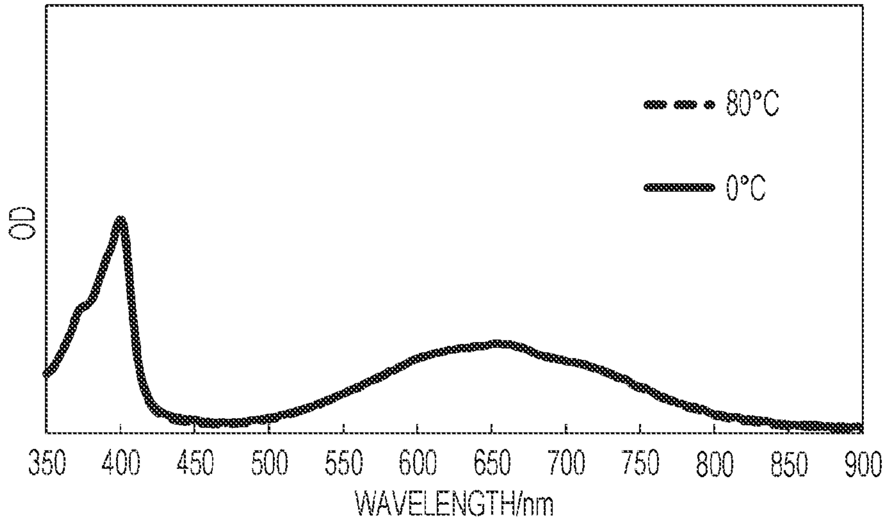
FIG. 8 is a graph showing ultraviolet-visible absorption spectra of exemplary compound A-3 in a colored state at 80° C. and 0° C.

For the element produced in Example 5, the spectrum in a radically colored state was measured at ambient temperatures of 0° C. and 80° C. The obtained spectra were normalized at 660 nm at which an absorption peak at 80° C. was observed. FIG. 8 shows ultraviolet-visible absorption spectra of the element produced in Example 8.

In the environments at 0° C. and 80° C., the change in the absorption spectrum due to the environmental temperature was small in the organic compound according to the present disclosure, showing that a color difference due to ambient temperature is unlikely to occur in the organic compound.

Comparative Example 1 (Temperature Characteristic Evaluation of Electrochromic Element Using Comparative Compound 1)

Figure 9:
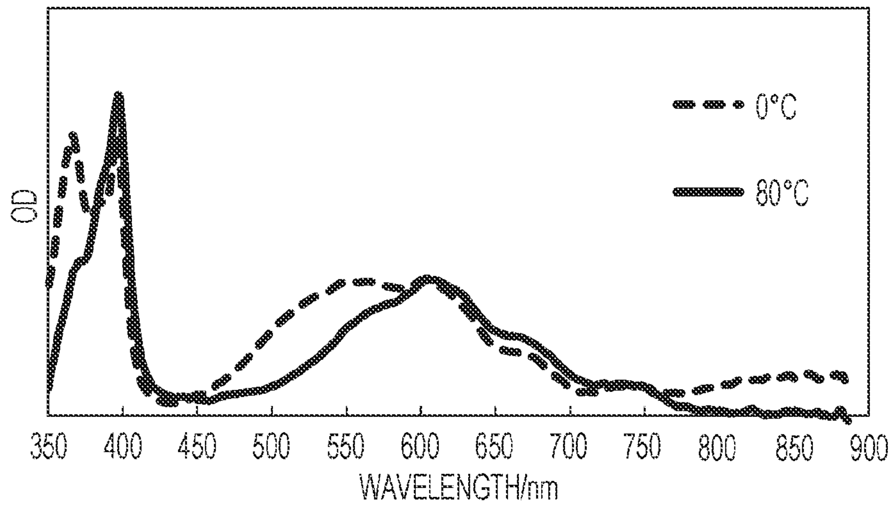
FIG. 9 is a graph showing ultraviolet-visible absorption spectra of comparative compound 1 in a colored state at 80° C. and 0° C.

An element was produced by the same method as in Example 5 except that comparative compound 1 was used instead of exemplary compound A-3 in Example 8. For the produced element, the spectrum in a radically colored state was measured at ambient temperatures of 0° C. and 80° C. The obtained spectra were normalized at 606 nm at which an absorption peak at 80° C. was observed. FIG. 9 shows the results. In the environments at 0° C. and 80° C., the change in the absorption spectrum due to the environmental temperature was large, and a color difference due to ambient temperature was observed.

Comparative compound 1

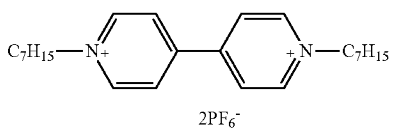

Example 9 and Comparative Examples 2 to 4 (Evaluation of Reduction Potential of Electrochromic Element)

Tetrabutylammonium hexafluorophosphate serving as an electrolyte was dissolved at a concentration of 0.1 M in propylene carbonate, and exemplary compound B-1 was dissolved at a concentration of 40.0 mM.

The measurement was conducted with an electrochemical analyzer model 832B available from BAS Inc. The measurement was conducted using carbon as a working electrode, platinum as a counter electrode, a $Ag/Ag^+$ electrode (propylene carbonate solution of silver hexafluorophosphate) as a reference electrode, and ferrocene as an internal standard.

Comparative compound 2

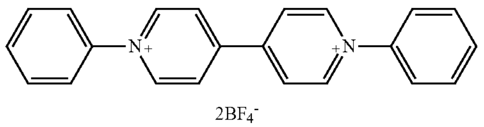

Comparative compound 3

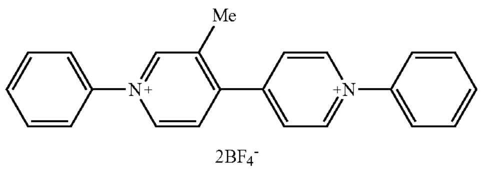

Comparative compound 4

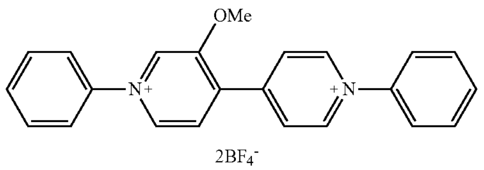

To compare the reduction potential, propylene carbonate solutions of comparative compounds 2 to 4 with a concentration of 40.0 mM were prepared by the same method and subjected to the measurement.

TABLE 1

| | Compound | Reduction potential |
|---|---|---|
| Example 9 | Exemplary compound B-1 | −0.62 V |
| Comparative Example 2 | Comparative compound 2 | −0.66 V |
| Comparative Example 3 | Comparative compound 3 | −0.77 V |
| Comparative Example 4 | Comparative compound 4 | −0.74 V |

The organic compound according to the present disclosure has a fluorine atom at the 3-position of 4,4'-bipyridine; therefore, the organic compound has a larger reduction potential (smaller absolute value of the reduction potential) than the unsubstituted compound, the compound substituted with a methyl group, and the compound substituted with a methoxy group. Accordingly, the compound according to the present disclosure is reduced more easily than the other compounds and thus can be driven as an EC element at a lower voltage.

As described above, since the organic compound according to the present disclosure has a large reduction potential (small absolute value of the reduction potential), the organic compound is a compound that exhibits an EC property at a lower voltage. Furthermore, the organic compound according to the present disclosure is a compound that can reduce a change in the absorption spectrum due to a change in the environmental temperature. In addition, the use of the organic compound according to the present disclosure in an EC element enables the EC element to be driven at a lower voltage and to have high transparency in the bleached state.

According to the present disclosure, an organic compound that exhibits an EC property at a lower voltage can be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-056594 filed Mar. 30, 2022, which is hereby incorporated by reference herein in its entirety.

What is claimed is:

1. An organic compound represented by formula (1):

(1)

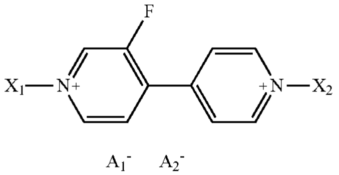

wherein, in formula (1), $X_1$ and $X_2$ are each independently selected from the group consisting of a substituted or unsubstituted alkyl group, a substituted or unsubstituted aryl group, and a substituted or unsubstituted aralkyl group; and $A_1^-$ and $A_2^-$ each independently represent a monovalent anion.

2. The organic compound according to claim 1, wherein, in formula (1), $X_1$ and $X_2$ have an alkyl group having 1 to 8 carbon atoms, an aryl group having 6 to 14 carbon atoms, or an aralkyl group having 7 to 10 carbon atoms.

3. The organic compound according to claim 1, wherein, in formula (1), $X_1$ and $X_2$ have a n-heptyl group, a phenyl group, or a benzyl group.

4. The organic compound according to claim 1, wherein, in formula (1), $X_1$ and $X_2$ have the same structure.

5. The organic compound according to claim 1, wherein, in formula (1), $A_1^-$ and $A_2^-$ are each independently selected from the group consisting of $PF_6^-$, $ClO_4^-$, $BF_4^-$, $CF_3SO_3^-$, $(CF_3SO_2)_2N^-$, $Br^-$, and $I^-$.

6. The organic compound according to claim 1, wherein, in formula (1), $A_1^-$ and $A_2^-$ are each independently selected from the group consisting of $PF_6^-$ and $BF_4^-$.

7. The organic compound according to claim 1, wherein, in formula (1), $A_1^-$ and $A_2^-$ represent the same anion.

8. The organic compound according to claim 1, wherein, in formula (1), $X_1$ and $X_2$ have an ionic group, an adsorptive group, or an acid ester group.

9. The organic compound according to claim 8, wherein, in formula (1), the ionic group, the adsorptive group, or the acid ester group has a carboxyl group, a sulfonic acid group, a phosphonic acid group, a trialkoxysilyl group, a carboxylic acid ester group, a sulfonic acid ester group, a phosphonic acid ester group, a pyridinium group, or a quinolinium group.

10. The organic compound according to claim 1, wherein, in formula (1), $X_1$ and $X_2$ have a phosphonic acid group, a carboxylic acid ester group, a phosphonic acid ester group, or a pyridinium group.

11. An electrochromic element comprising:
- a pair of electrodes; and
- an electrochromic layer disposed between the pair of electrodes,
- wherein the electrochromic layer contains the organic compound according to claim 1.

12. The electrochromic element according to claim 11, wherein the electrochromic layer contains the organic compound and a second organic compound.

13. The electrochromic element according to claim 12, wherein the second organic compound is selected from the group consisting of a phenazine-based compound, a metallocene-based compound, a phenylenediamine-based compound, and a pyrazoline-based compound.

14. The electrochromic element according to claim 11, wherein the electrochromic layer further contains an electrolyte.

15. The electrochromic element according to claim 11, wherein the electrochromic layer further contains a thickener.

16. The electrochromic element according to claim 15, wherein the thickener is polymethyl methacrylate, polyethylene oxide, or polypropylene oxide.

17. An optical filter comprising:
- the electrochromic element according to claim 11; and
- an active element connected to the electrochromic element.

18. The optical filter according to claim 17, wherein the active element drives the electrochromic element to adjust an amount of light passing through the electrochromic element.

19. A lens unit comprising:
- the optical filter according to claim 17; and
- an image pickup optical system having a plurality of lenses.

20. An image pickup apparatus comprising:
- the optical filter according to claim 17; and
- an image pickup element configured to receive light that has passed through the optical filter.

21. A window comprising:
- a pair of substrates;
- the electrochromic element according to claim 11 disposed between the pair of substrates; and
- an active element connected to the electrochromic element.

22. An electrochromic mirror comprising:
- a pair of substrates;
- the electrochromic element according to claim 11 disposed between the pair of substrates;
- an active element connected to the electrochromic element; and
- a reflective member.

* * * * *